United States Patent [19]

Herbert

[11] 4,175,555

[45] Nov. 27, 1979

[54] BONE SCREW

[75] Inventor: Timothy J. Herbert, Redfern, Australia

[73] Assignee: Interfix Limited, Hong Kong, Hong Kong

[21] Appl. No.: 880,099

[22] Filed: Feb. 22, 1978

[30] Foreign Application Priority Data

Feb. 24, 1977 [AU] Australia ............... PC9179

[51] Int. Cl.² ............... A61F 5/04; A61B 17/18
[52] U.S. Cl. ............... 128/92 B; 128/84 R; 85/42; 85/47
[58] Field of Search ............ 128/92 B, 92 BB, 92 BC, 128/92 R, 92 D, 92 G, 84 R; 85/42, 46, 47

[56] References Cited

U.S. PATENT DOCUMENTS

| 146,023 | 12/1873 | Russell ............... 85/46 |
| 2,801,631 | 8/1957 | Charnley ............... 128/92 BB |

FOREIGN PATENT DOCUMENTS

| 731381 | 4/1966 | Canada ............... 85/42 |
| 365613 | 12/1938 | Italy ............... 128/92 BB |

OTHER PUBLICATIONS

"Illustrations for the Introduction of the Lorenzo Lag Screw" DePuy Fracture Appliances & their Application (catalog), DePuy Mfg. Co., Warsaw, Ind. pp. 46–48.

*Primary Examiner*—Ronald L. Frinks
*Attorney, Agent, or Firm*—Pravel, Gambrell, Hewitt, Kirk, Kimball & Dodge

[57] ABSTRACT

A bone screw is provided with screw threads which are like-handed but of different pitch on its respective leading and trailing ends. In the more favored embodiment, the pitch of the leading screw thread exceeds that of the trailing screw thread. Such a screw may be used to hold portions of a fractured bone in compressive engagement.

4 Claims, 5 Drawing Figures

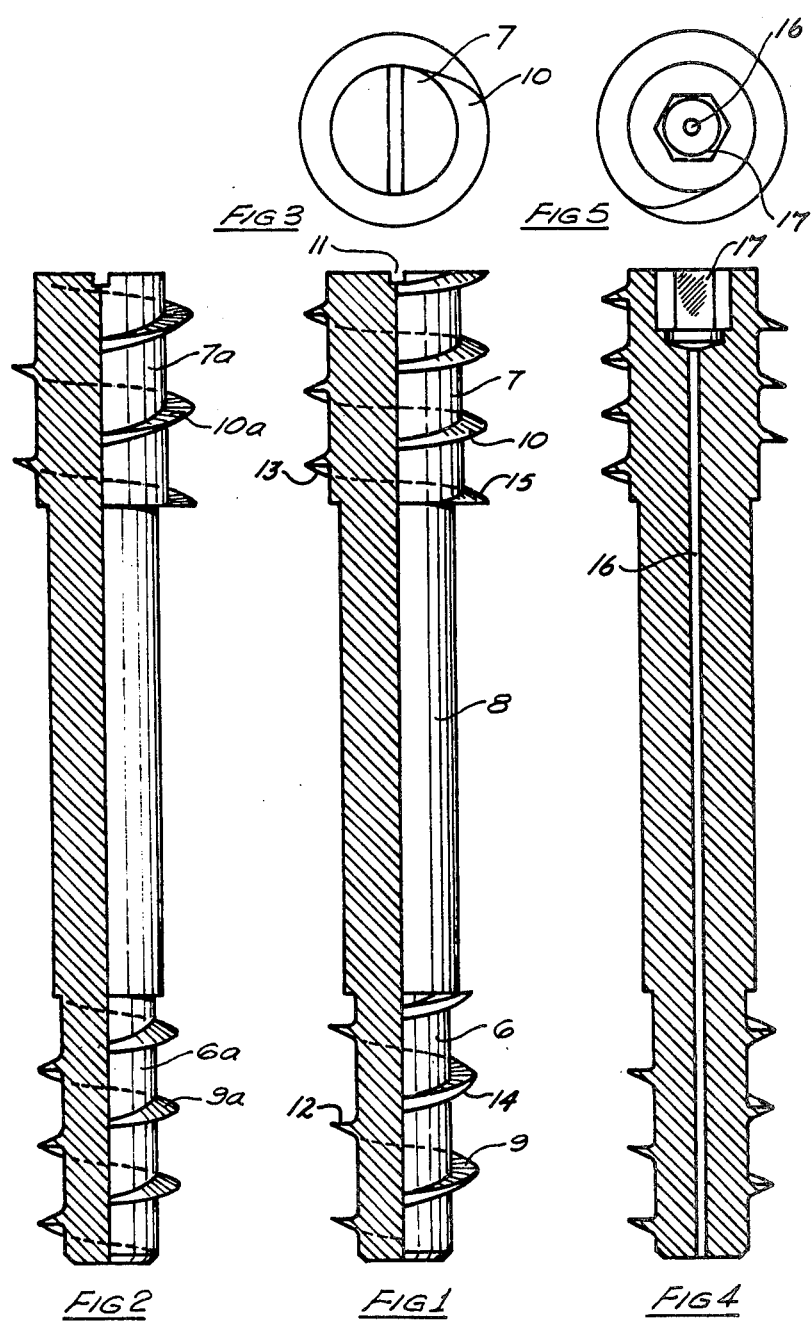

BONE SCREW

BACKGROUND OF THE INVENTION

This invention relates to bone screws; that is, those surgical fastenings by which two pieces of bone may be held together. Although usable in many forms of bone connection, bone screws of the kind under consideration, while not restricted thereto, are particularly useful in cross fixation of fractured or severed bone fragments.

In almost all bone connections of the kind under consideration, it is essential for the fractured surfaces to be united to be brought into closely contacting mutual confrontation. This intimacy of contact is usually referred to as "compression". The actual need is for the fractured surfaces to be in close, well-fitting contact and to be so held during the healing process. In practice, the simplest way of ensuring this close contact is, where practicable, to apply a compressive loading to the bone portions in a direction substantially normal to the fracture faces.

Hitherto, standard bone screws have been of two typical forms. One of these has a thread only at its leading end, the head at the trailing end being separated from the thread by a smooth, cylindrical shank. It will be clear that such a bone screw, by threading wholly in the remote bone fragment and extending freely through the near fragment, can provide compressive action upon the fractured faces to be united.

The second type of bone screw has a stem or shaft threaded over its full length. Such a screw can only be used to apply compression between two bone fragments if the near fragment is "over drilled" so that the thread engages solely in the remote fragment, the near fragment being free to move over the stem of the screw during insertion.

In both these cases it will be clear that this gaining of compressive action is achieved at the expense of subjecting the bone surface immediately below the screw head to concentrated bearing loads, and also at the expense of the screw head constituting a relatively large protrusive element.

It is not uncommon for the standard type of bone screw to be used with washers or other metallic inserts between the screw head and the adjacent bone surface. Any such inclusions are likely to provide some degree of load spreading which would relieve bearing stress intensity on the bone surface. But this load spreading facility is often insufficient because bone surfaces are very rarely flat and even where a washer or other insert is provided (unless speciallymoulded closely to fit the bone), the bearing pressure exerted by the screw head remains, in effect, a highly concentrated load and crumbling or other failure of the adjacent bone affected frequently occurs without sufficient compressive action at the fractured faces being achieved.

The standard type of bone screw has several other shortcomings. For example, the near bone fragment is held relative to the remote portion purely by compressive forces which act in the line of the screw; the screw head merely abutting the cortical surface of the near fragment as distinct from being firmly and securely anchored to that fragment. If the cortical bone layer directly under the screw head provides inadequate support either during insertion or subsequently, then compression is lost and the near bone fragment is free to move relative to the trailing part of the screw. In consequence, relative movement between the bone portions to be held can occur.

A further adverse factor is that of bone resorption. This may be a physiological response to localized pressure and may occur either directly under the screw head or at the fracture site. Clearly, where such resorption occurs, loosening of the screw may also arise, with subsequent movement of the bone fragments.

SUMMARY OF THE INVENTION

The object of this invention is to overcome or ameliorate the shortcomings indicated above in a very simple but highly effective manner.

The invention provides a bone screw consisting of:
(a) a shaft comprising leading and trailing portions;
(b) a first screw thread on said leading portion;
(c) a second screw thread on said trailing portion which, relative to said first screw thread, is like-handed but of different pitch; and
(d) means on the distal end of said trailing portion to accommodate a tool for driving the screw; said screw being further characterized in that its cross sectional diameter is nowhere greater along the length thereof than the crest diameter of the screw thread of said trailing portion.

Far more usually, screws according hereto will be required to provide compressive action as referred to above; and, this being so, the pitch of the first or leading end screw-thread will slightly exceed that of the second or trailing end thread. In some situations in orthopaedic surgery, it may be desired to apply distraction between two bone fragments as distinct from compressive action as referred to above. The screws hereof may be suited to this distraction purpose by making the pitch of the trailing end thread greater than that of the leading end thread.

BRIEF DESCRIPTION OF THE DRAWINGS

Examples of the invention are illustrated in the drawings herewith. All of the figures are drawn on an oversized scale, and like structure in different figures bears like reference numerals.

FIG. 1 is a side elevation, half in section, of a compression bone screw;

FIG. 2 is a similar view of a distraction bone screw;

FIG. 3 is a plan projected from FIG. 2;

FIG. 4 is a side elevation, half in section, of a cannulated, compression bone screw; and FIG. 5 is a plan projected from FIG. 4.

DESCRIPTION OF THE PREFERRED EMBODIMENT

Referring to FIG. 1, the shaft of the screw comprises leading end portion 6 and a trailing end portion 7 axially spaced apart by a substantially cylindrical shank 8. The leading end portion is furnished with first screw thread 9 and the trailing end portion has a second screw thread 10. The threads 9 and 10 are like-handed. This screw is intended to be one for applying compressive action, hence the pitch of thread 9 is slightly greater than that of thread 10. As will be seen from FIG. 1, the trailing end of the bone screw is furnished with a transverse slot 11 to which a screw driver or the like may be applied.

The screw illustrated in FIG. 1 is intended principally to engage the cancellous or spongy inner tissue of a bone. Accordingly, both of its threads are of a form which may be described as acute backed buttess type; in that the thread helices have pressure faces 12 and 13 which are substantially normal to the longitudinal axis of the screw and backing surfaces 14 and 15, which are relatively acute. It will be noticed from the drawing that the bearing faces 12 and 13 are in mutually confronting disposition, so as to provide, as much as possible, bone loading forces parallel to the longitudinal axis of the screw. It will be understood, however, that the invention is in no way limited to this or any other thread form.

In using a screw according hereto, it is first necessary to select a screw length suited to the task in hand. A short entry bore of diameter approximately equal to the root diameter of trailing end portion 7 is drilled into the near bone fragment to a sufficient depth to accommodate that portion. A bore of diameter approximately equal to the root diameter of leading end portion 6 is then drilled coaxially with the first mentioned bore through the near bone fragment, through the fracture inter-face and into the remote bone fragment; the drilling into the remote bone fragement being at least sufficient in depth to accept the screw leading end portion 6. Before the screw is inserted, the second mentioned bore is preferably tapped with a tap suitable for the thread on leading end portion 6.

When engagement is established, continued turning of the screw will tend to cause the leading edge of the screw to advance axially into the remote fragment to a slightly greater extent than it does relative to the near fragment. This puts the screw in tension and hence the fracture faces under compression.

It will be appreciated that an important aspect of the present invention resides in the absence of a conventional head on the trailing end portion 7. This is valuable in many situations of bone screw use because screw head protrussion is avoided; and the threaded trailing end of the screw can be wholly sunken into the bone tissue. This in turn allows, for example, the screw to be inserted through the cartilage of a joint surface and buried beneath that surface so that the joint and its use would be unaffected by the presence of the bone screw. In other words, where hitherto a bone screw could not be applied through cartilage owing to the protrusive presence of a screw head within the joint, a screw according to the present invention may be effectively used in that location without impairing resumption of the normal joint relationship and without break or hindrance to full re-establishment of the cartilage over the rubbing surfaces of the joint.

The screw shown in FIGS. 2 and 3 is virtually the same in structure as that shown in FIG. 1 except for the leading end portion 6a having a thread 9a whereof the pitch is slightly less than that of the thread 10a of the trailing end portion 7a. Hence, this screw is a distraction screw; that is, one which, when tightened, tends to hold the joined bone fragments slightly spaced apart or at least not firmly pressed each towards the other.

The screw shown in FIGS. 4 and 5 is virtually the same in structure as that shown in FIG. 1 except for being provided with a cannula or lumen 16 to provide for use of a guide wire in those cases where such is required. This embodiment also illustrates the provision of a hexagonal well 17, to receive a key spanner, instead of a screw driver slot such as that shown, at 11, in FIG. 1. It is to be noted, as can be ascertained in the drawings, that each of the screws set forth in the drawings is characterized by the structural feature that each has is cross-sectional diameter is nowhere greater along the length thereof that the crest diameter of the screw thread 10 (or 10a) of the trailing portion 7 (or 7a).

The foregoing description of the present invention is illustrative and explanatory thereof and various changes in the size, shape and materials as well as in the details of the preferred embodiment of the illustrated construction thereof may be made without departing from the spirit of the invention.

I claim:

1. A bone screw for connecting a fractured portion of a bone to a parent bone, comprising:
    (a) a shaft comprising a leading end portion, a trailing end portion and a central unthreaded portion;
    (b) said central portion spacing said end portions apart and being axially longer than either of said end portions;
    (c) a first uniformly pitched screw-thread on said leading end portion;
    (d) a second uniformly pitched screw-thread on said trailing end portion, which relative to said first screw-thread, is like-handed but of different pitch;
    (e) said second uniformly pitched screw-thread extending radially wholly beyond the circumference of said central portion, and the crest diameter of said second thread being greater than the diameter of any other part of the screw, thereby to adapt the screw for entire encasement within the bone portions to be connected thereby;
    (f) both of said threads being adapted to thread in the cancellous material of the respective bone portions to be joined by the screw; and
    (g) means on the trailing end of said trailing portion to accommodate a tool for driving the screw.

2. A bone screw according to claim 1, wherein the pitch of said first uniformly pitched screw thread is greater than that of said second uniformly pitched screw thread.

3. A bone screw according to claim 1, wherein the pitch of said first uniformly pitched screw thread is less than that of said second uniformly pitched screw thread.

4. A bone screw according to claim 1, wherein said shaft has a cannula throughout its axial length.

* * * * *